United States Patent
Larson et al.

(10) Patent No.: US 9,192,432 B2
(45) Date of Patent: Nov. 24, 2015

(54) LEVER LATCH ASSEMBLIES FOR SURGICAL IMPROVEMENTS

(75) Inventors: Eric R. Larson, Boulder, CO (US);
John J. Kappus, Denver, CO (US);
Wayne Siebrecht, Golden, CO (US)

(73) Assignee: Covidien LP, Mansfield, MA (US)

( * ) Notice: Subject to any disclaimer, the term of this patent is extended or adjusted under 35 U.S.C. 154(b) by 777 days.

(21) Appl. No.: 13/482,589

(22) Filed: May 29, 2012

(65) Prior Publication Data
US 2013/0325057 A1    Dec. 5, 2013

(51) Int. Cl.
*A61B 17/00* (2006.01)
*A61B 18/14* (2006.01)
*A61B 19/00* (2006.01)
*A61B 18/00* (2006.01)
*A61B 18/12* (2006.01)

(52) U.S. Cl.
CPC ... *A61B 18/1445* (2013.01); *A61B 2018/00309* (2013.01); *A61B 2018/1226* (2013.01); *A61B 2018/1455* (2013.01); *A61B 2019/4857* (2013.01)

(58) Field of Classification Search
CPC .................. A61B 18/1445; A61B 2018/00309; A61B 2018/1455; A61B 2019/4857; A61B 2018/00601; A61B 17/29; A61B 17/2909; A61B 17/320016; A61B 18/085
USPC ............................. 606/205, 32, 39, 45, 51, 52
See application file for complete search history.

(56) References Cited

U.S. PATENT DOCUMENTS

| | | | |
|---|---|---|---|
| D249,549 S | 9/1978 | Pike | |
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |

(Continued)

FOREIGN PATENT DOCUMENTS

| CN | 201299462 | 9/2009 |
|---|---|---|
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Katherine M Shi

(57) ABSTRACT

A surgical instrument includes a handle movable between first and second positions for transitioning an end effector assembly between states and to a third position for returning the handle. A latch arm coupled to the handle includes one or more engagement members. A latch block defines a guide track having a latching path configured to guide the engagement member(s) therealong, an engagement portion configured to engage the engagement member(s) to latch the handle in the second position, and a return path configured to guide the engagement member(s) therealong. A first step interdisposed between the latching path and engagement portion guides the engagement member(s) into engagement with the engagement portion and inhibits the engagement member(s) from returning along the latching path. A second step interdisposed between the engagement portion and the return path guides the engagement member(s) along the return path and inhibits the engagement member(s) from re-engaging the engagement portion.

6 Claims, 9 Drawing Sheets

(56) References Cited

U.S. PATENT DOCUMENTS

| | | |
|---|---|---|
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| 5,800,449 A | 9/1998 | Wales |
| 5,827,279 A | 10/1998 | Hughett et al. |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,083,618 B2 | 8/2006 | Couture et al. |
| 7,090,673 B2 | 8/2006 | Dycus et al. |
| 7,101,371 B2 | 9/2006 | Dycus et al. |
| D531,311 S | 10/2006 | Guerra et al. |
| D533,274 S | 12/2006 | Visconti et al. |
| D533,942 S | 12/2006 | Kerr et al. |
| 7,150,749 B2 | 12/2006 | Dycus et al. |
| D535,027 S | 1/2007 | James et al. |
| 7,156,846 B2 | 1/2007 | Dycus et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| 7,384,420 B2 | 6/2008 | Dycus et al. |
| D575,395 S | 8/2008 | Hushka |
| D575,401 S | 8/2008 | Hixson et al. |
| D582,038 S | 12/2008 | Swoyer et al. |
| 7,473,253 B2 | 1/2009 | Dycus et al. |
| 7,597,693 B2 | 10/2009 | Garrison |
| 7,628,791 B2 | 12/2009 | Garrison et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,070,748 B2 | 12/2011 | Hixson et al. |
| D661,394 S | 6/2012 | Romero et al. |
| 8,241,282 B2 | 8/2012 | Unger et al. |
| 8,241,284 B2 | 8/2012 | Dycus et al. |
| 2009/0012520 A1 | 1/2009 | Hixson et al. |
| 2009/0182327 A1 | 7/2009 | Unger |
| 2010/0145334 A1 | 6/2010 | Olson et al. |
| 2010/0280515 A1 | 11/2010 | Hixson et al. |
| 2012/0184989 A1* | 7/2012 | Twomey .................. 606/206 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1486177 A1 | 12/2004 |
| EP | 1642543 A1 | 4/2006 |
| EP | 1810625 B1 | 8/2009 |
| EP | 2105104 A2 | 9/2009 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |

(56) References Cited

FOREIGN PATENT DOCUMENTS

| SU | 401367 | 11/1974 |
|---|---|---|
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 920, 2000, Thomas P. Ryan.
U.S. Appl. No. 12/336,970, filed Dec. 17, 2008, Paul R. Sremeich.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/464,569, filed May 4, 2012, Duane E. Kerr.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,543, filed May 14, 2012, Sean T. Dycus.
U.S. Appl. No. 13/470,775, filed May 14, 2012, James D. Allen, IV.
U.S. Appl. No. 13/470,797, filed May 14, 2012, John J. Kappus.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/488,093, filed Jun. 4, 2012, Kristin D. Johnson.
U.S. Appl. No. 13/491,853, filed Jun. 8, 2012, Jessica E. Olson.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/550,322, filed Jul. 16, 2012, John J. Kappus.
U.S. Appl. No. 13/571,055, filed Aug. 9, 2012, Paul Guerra.
U.S. Appl. No. 13/571,821, filed Aug. 10, 2012, Joseph D. Bucciaglia.
U.S. Appl. No. 13/584,194, filed Aug. 13, 2012, Sean T. Dycus.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

(56) References Cited

OTHER PUBLICATIONS

Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.

(56) References Cited

OTHER PUBLICATIONS

Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 006233.8 dated Feb. 2, 2012.
Int'l Search Report EP 11 007972.0 dated Dec. 28, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 168419.7 dated Oct. 20, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

\* cited by examiner

LEVER LATCH ASSEMBLIES FOR SURGICAL IMPROVEMENTS

BACKGROUND

1. Technical Field

The present disclosure relates to surgical instruments and, more particularly, to lever latch assemblies for use with surgical instruments, e.g., forceps, for grasping, treating, and/or dividing various tissue structures.

2. Background of Related Art

A forceps is a plier-like instrument which relies on mechanical action between its jaws to grasp, clamp, and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control, and gap distance (i.e., distance between opposing jaw members when closed about tissue) to "seal" tissue, vessels, and certain vascular bundles. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any of the other aspects described herein.

In accordance with aspects of the present disclosure, a surgical instrument is provided including a movable handle, an end effector assembly, and a latch assembly. The movable handle is movable between a first position and a second position for transitioning the end effector assembly between a first state and a second state. The movable handle is further movable from the second position to a third position to permit return of the movable handle to the first position. The latch assembly includes a latch arm and a latch block. The latch arm is coupled to the movable handle at a first end thereof and includes one or more engagement members disposed at a second end thereof. The latch block defines a guide track therein that is configured to receive the engagement member(s) therein. The guide track includes a latching path configured to guide translation of the engagement member(s) therealong upon movement of the movable handle from the first position to the second position, an engagement portion configured to engage the engagement member(s) upon achieving the second position to latch the movable handle in the second position, and a return path configured to guide translation of the engagement member(s) therealong upon movement of the movable handle from the second position to the third position and back to the first position. A first step is interdisposed between the latching path and the engagement portion such that, upon movement of the movable handle to the second position, the engagement member(s) is guided into engagement with the engagement portion and is inhibited from returning along the latching path. A second step is interdisposed between the engagement portion and the return path such that, upon movement of the movable handle to the third position, the engagement member(s) is guided along the return path and is inhibited from returning to engagement with the engagement portion.

In one aspect, the movable handle is coupled to a drive assembly and is movable from the first position to the second position to translate the drive assembly relative to the end effector assembly to transition the end effector assembly between the first and second states.

In another aspect, the end effector assembly includes first and second jaw members, one or both of which is movable relative to the other between a spaced-apart position and an approximated position for grasping tissue therebetween.

In another aspect, the latch arm defines a bifurcated second end including first and second engagement members coupled to one another. The first and second engagement members are configured to move relative to one another from a neutral position, wherein the first and second engagement members define a first distance therebetween, to a loaded position, wherein the first and second engagement members define a second distance therebetween, upon translation along the latching path. The first and second engagement members are further configured to return to the neutral position upon traversing the first step.

In yet another aspect, the first and second engagement members are configured to move relative to one another from the neutral position to the loaded position upon disengagement from the engagement portion and to return to the neutral position upon traversing the second step.

In still another aspect, the first and second engagement members are coupled via a living hinge configured to bias the first and second engagement members towards the neutral position.

A surgical instrument provided in accordance with other aspects of the present disclosure includes a movable handle movable between a first position and a second position for transitioning an end effector assembly between a first state and a second state. The movable handle is further movable from the second position to a third position to permit return of the movable handle to the first position. A latch assembly includes a latch arm and a latch block. The latch arm is coupled to the movable handle at a first end thereof and includes one or more engagement members disposed at a second end thereof. The latch block defines a guide track therein that is configured to receive the engagement member(s) therein. The latch block includes an engagement portion configured to engage the engagement member(s) upon movement of the movable handle to the second position to latch the movable handle in the second position, and a plurality of flanges. Each flange is movable relative to the latch block between a neutral position, wherein the flange is generally co-planar with a surface of the latch block, and a loaded position, wherein the flange extends from the surface of the latch block. One of the plurality of flanges is configured to move from the neutral position towards the loaded position upon movement of the movable handle from the first position towards the second position and to return to the neutral position once the movable handle has achieved the second position to guide the engagement member(s) into engagement with the engagement portion and to inhibit the movable handle from returning to the first position. Another of the plurality of flanges is configured to move from the neutral position towards the loaded position upon movement of the movable handle from the second position towards the third position and to return to the neutral position once the movable handle has achieved the third position to inhibit the engagement member(s) from re-engaging the engagement portion and to permit the movable handle to return to the first position.

In one aspect, the movable handle is coupled to a drive assembly such that movement of the movable handle from the first position to the second position translates the drive assembly relative to the end effector assembly to transition the end effector assembly between the first and second states.

In another aspect, the end effector assembly includes first and second jaw members, one or both of which is movable relative to the other between a spaced-apart position and an approximated position for grasping tissue therebetween.

In still another aspect, each flange is coupled to the latch block via a living hinge and is biased by the respective living hinge towards the neutral position.

In yet another aspect, the engagement member(s) is translated along a first flange upon movement of the movable handle from the first position towards the second position to urge the first flange from the neutral position towards the loaded position, and is positioned beyond the first flange once the movable handle has achieved the second position, allowing the first flange to return to the neutral position to inhibit backtracking therealong.

In still yet another embodiment, the engagement member(s) is translated along a second flange upon movement of the movable handle from the second position towards the third position to urge the second flange from the neutral position towards the loaded position, and is positioned beyond the second flange once the movable handle has achieved the third position, allowing the second flange to return to the neutral position to inhibit backtracking therealong.

Also provided in accordance with aspects of the present disclosure is another surgical instrument including a movable handle movable between a first position and a second position for transitioning an end effector assembly between a first state and a second state. The movable handle is further movable from the second position to a third position to permit return of the movable handle to the first position. A latch assembly includes a latch arm and a plurality of ribs. The latch arm is coupled to the movable handle at a first end thereof and includes one or more engagement members disposed at a second end thereof. The plurality of ribs is arranged to define a guide track. More specifically, a first rib is configured to be contacted by the engagement member(s) upon movement of the movable handle from the first position to the second position such that audible and/or tactile feedback is provided indicating that the second position has been achieved. A second rib is configured to engage the engagement member(s) therein for latching the movable handle in the second position once the second position has been achieved. A third rib is configured to be contacted by the engagement member(s) upon movement of the movable handle from the second position to the third position such that audible and/or tactile feedback is provided indicating that the third position has been achieved.

In one aspect, the movable handle is coupled to a drive assembly such that movement of the movable handle from the first position to the second position translates the drive assembly relative to the end effector assembly to transition the end effector assembly between the first and second states.

In another aspect, the end effector assembly includes first and second jaw members, one or both of which is movable relative to the other between a spaced-apart position and an approximated position for grasping tissue therebetween.

In still another aspect, the ribs are monolithically formed with and extend inwardly into a housing of the surgical instrument.

In yet another aspect, the first rib is further configured to inhibit the engagement member(s) from over-shooting the second rib.

In still yet another aspect, the latch arm is spring-biased such that the engagement member(s) is biased into contact with the first rib to provide the feedback thereof and such that the engagement member(s) is biased into contact with the third rib to provide the feedback thereof.

BRIEF DESCRIPTION OF THE DRAWINGS

Various aspects of the present disclosure are described herein with reference to the drawings wherein like reference numerals identify similar or identical elements.

DETAILED DESCRIPTION

The operating features and inter-cooperating components of surgical instruments provided in accordance with the present disclosure are shown in the Figures and described hereinbelow. More specifically, the surgical instruments are shown as forceps, e.g., forceps 10 (FIG. 1) or forceps 400 (FIG. 9), although the present disclosure is equally applicable for use with any other suitable surgical instrument having a handle assembly operable to control and/or manipulate an end effector assembly of the surgical instrument. Obviously, different connections and considerations apply to each particular type of instrument; however, the novel aspects with respect to the latch assemblies for selectively latching the handle assembly remain generally consistent regardless of the particular type of instrument used.

Figure 1A:
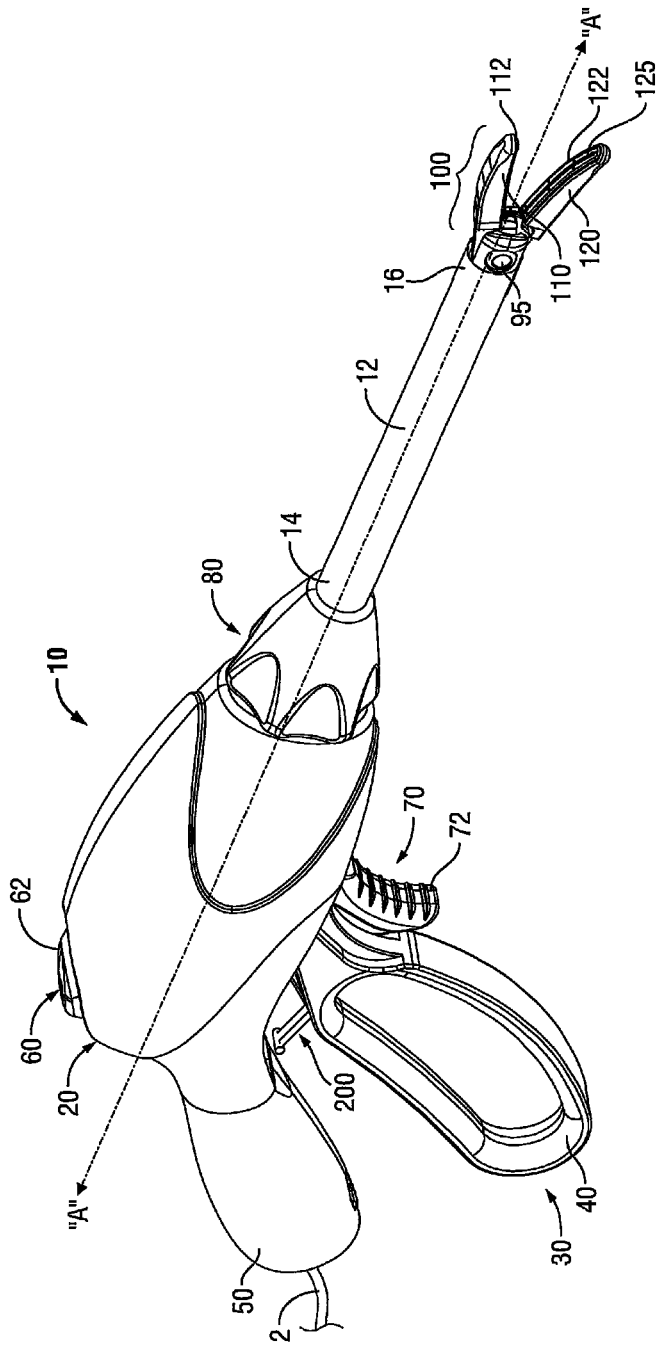
FIG. 1A is a side, perspective view of a forceps provided in accordance with the present disclosure wherein jaw members of the forceps are disposed in a spaced-apart position.
Figure 1B:
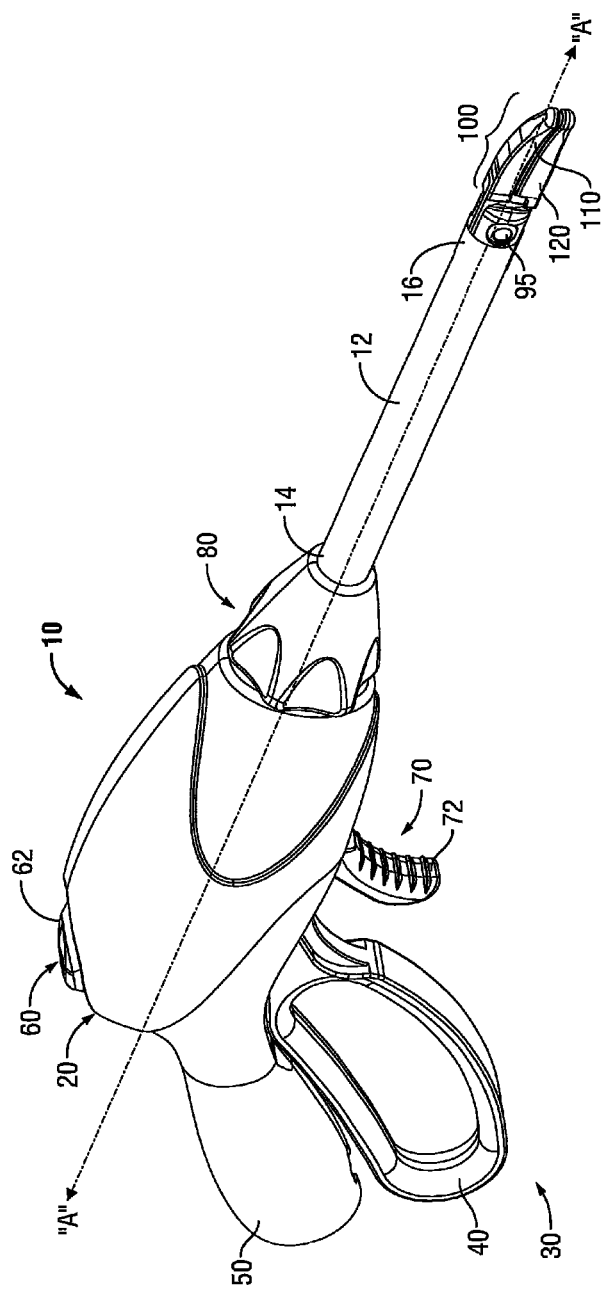
FIG. 1B is a side, perspective view of the forceps of FIG. 1A wherein the jaw members of the forceps are disposed in an approximated position.

Referring to FIGS. 1A-1B, one embodiment of a surgical instrument configured for use in accordance with the present disclosure for various surgical procedures is shown generally as forceps 10. Forceps 10 includes a housing 20, a handle assembly 30, a switch assembly 60, a trigger assembly 70, a rotating assembly 80, and an end effector assembly 100 that mutually cooperate to grasp, treat, and divide tubular vessels and vascular tissues. Forceps 10 further includes a shaft 12 having a distal end 16 configured to mechanically engage end effector assembly 100 and a proximal end 14 configured to mechanically engage housing 20. An electrosurgical cable 2 connects forceps 10 to an electrosurgical generator (not shown) such that, upon activation of switch 62 of switch assembly 60, energy is supplied to end effector assembly 100 to treat tissue grasped therein. Alternatively, forceps 10 may be configured as a battery-powered instrument having a portable battery (not shown) and generator (not shown) disposed within housing 20.

With continued reference to FIGS. 1A-1B, handle assembly 30 includes a fixed handle 50 and a movable handle 40. Fixed handle 50 is integrally associated with housing 20 and movable handle 40 is movable relative to fixed handle 50, as will be explained in greater detail below, to impart movement of jaw members 110 and 120 of end effector assembly 100 between a spaced-apart position (FIG. 1A) and an approximated position (FIG. 1B) to grasp tissue therebetween. As will be described in greater detail below, various embodiments of latch assemblies configured for latching movable handle 40 in one or more positions are provided for use with handle assembly 30 (or any other suitable handle assembly). Rotating assembly 80 is operatively associated with housing 20 and is rotatable about a longitudinal axis "A-A" to rotate end effector assembly 100 about longitudinal axis "A-A." Trigger 72 of trigger assembly 70 is selectively actuatable to deploy a knife 190 (FIG. 2) from shaft 12 to between jaw members 110, 120 to cut tissue grasped therebetween.

Figure 2:
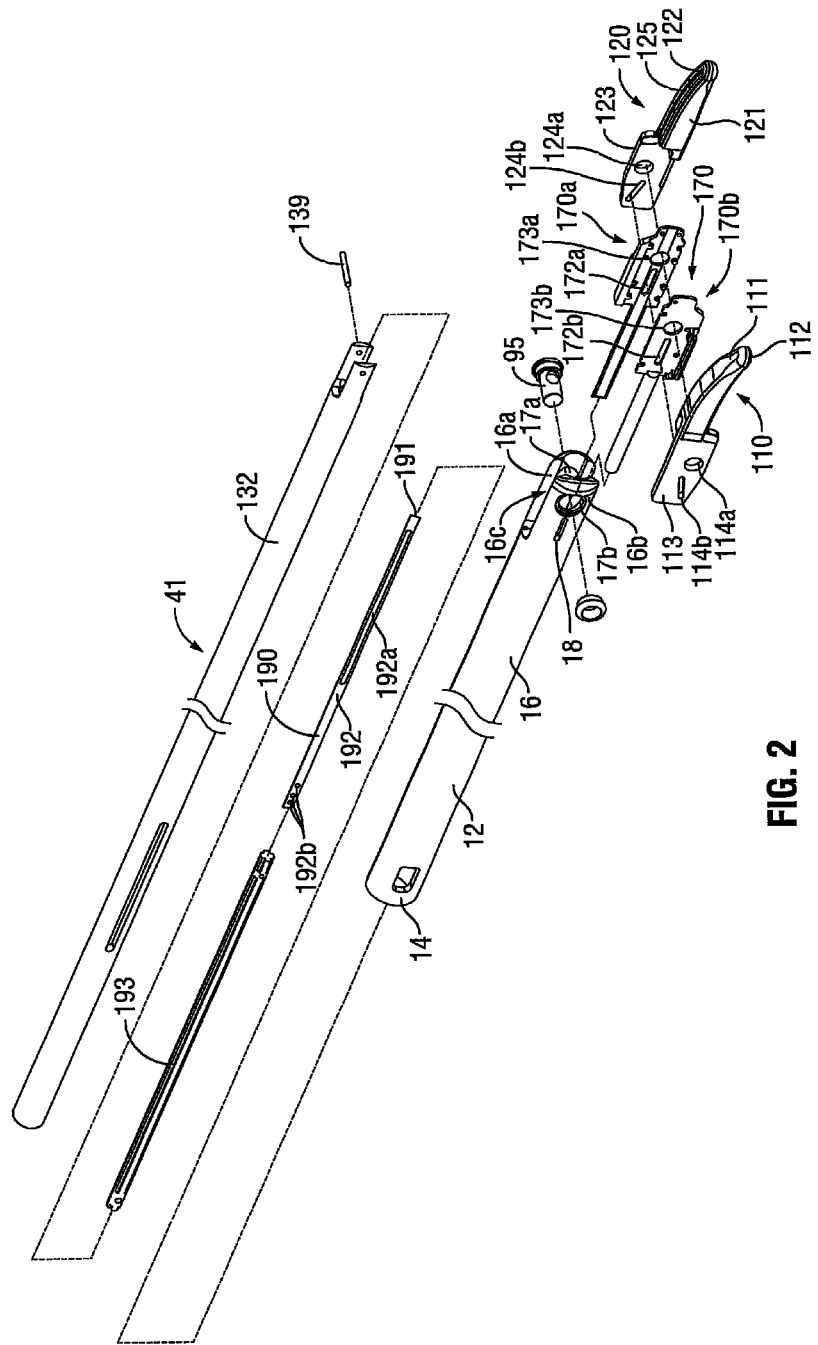
FIG. 2 is a side, perspective view of a distal portion of the forceps of FIG. 1A shown with parts separated.
Figure 3:
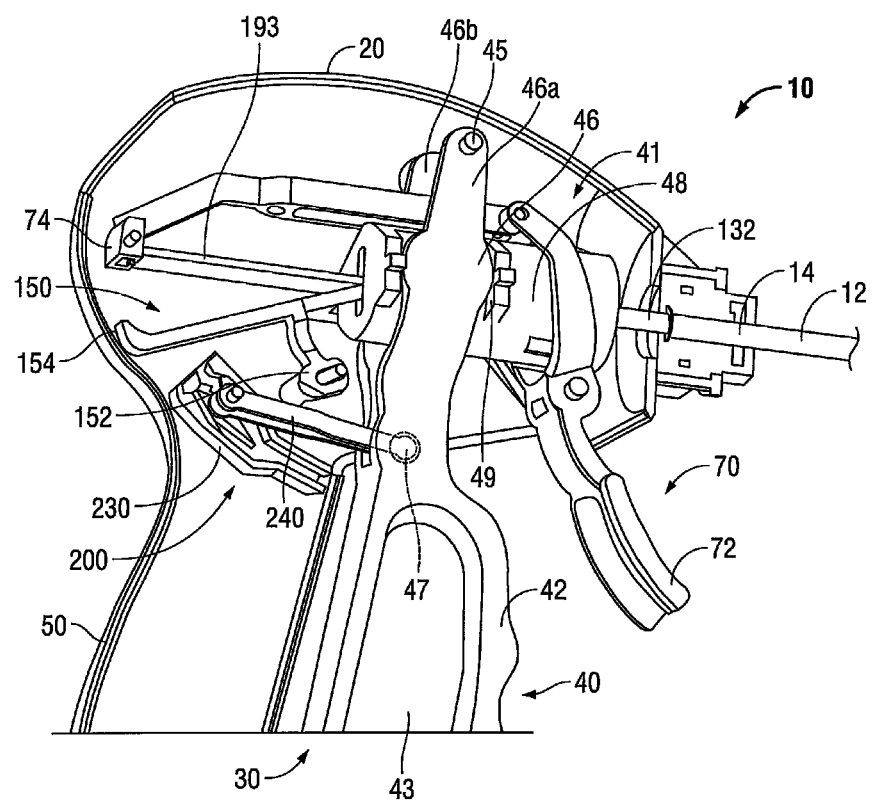
FIG. 3 is a side, perspective view of a proximal end of the forceps of FIG. 1A wherein a portion of a housing has been removed to show a latch assembly and the other internal components thereof.

Continuing with reference to FIGS. 1A-1B, and with additional reference to FIGS. 2-3, end effector assembly 100 is attached at distal end 16 of shaft 12 and includes a pair of opposing jaw members 110 and 120. End effector assembly 100 is designed as a bilateral assembly, i.e., both jaw members 110 and 120 are movable relative to one another and to shaft 12 about a pivot pin 95, although end effector assembly 100 may alternatively be configured as a unilateral end effector assembly. Further, jaw members 110 and 120 of end effector assembly 100 are curved to facilitate manipulation of tissue and to provide better "line of sight" for accessing targeted tissues, although other configurations may also be provided.

Each jaw member 110, 120 of end effector assembly 100 includes a distal jaw portion 111, 121 that supports an electrically-conductive tissue sealing plate 112, 122, respectively, thereon, and a proximal flange 113, 123 extending distally from the respective distal jaw portion 111, 121 for operably mounting jaw members 110, 120, respectively, at distal end 16 of shaft 12. Either or both electrically-conductive tissue sealing plates 112, 122 are adapted to connect to a source of energy, e.g., a generator (not shown), for conducting energy therebetween and through tissue grasped between jaw members 110, 120 to treat, e.g., seal, tissue. More specifically, wire(s) (not shown) may extend from electrosurgical cable 2 (FIGS. 1A-1B), through housing 20 and shaft 12, ultimately connecting to one or both of tissue sealing plates 112, 122 for providing energy thereto, although other configurations are also contemplated. Tissue sealing plates 112, 122 and distal jaw portions 111, 121 of one or both of jaw members 110, 120, respectively, cooperate to define a longitudinally-oriented knife channel 125 therein that is configured to permit reciprocation of a knife 190 therethrough to cut tissue grasped between jaw members 110, 120.

Proximal flanges 113, 123 of jaw members 110, 120, respectively, each include a pivot aperture 114a, 124a, respectively, defined therethrough, and an angled cam slot 114b, 124b, respectively, defined therethrough. End effector assembly 100 also includes a knife guide 170 that facilitates alignment and translation of knife 190 through knife channels 125 upon reciprocation of knife drive rod 193. Knife guide 170 includes first half 170a and second half 170b which mechanically interface to slidably encapsulate the knife 190 therein. First and second halves 170a and 170b each include a pivot aperture 173a, 173b, respectively, defined therethrough and a longitudinal cam slot 172a, 172b, respectively, defined therethrough.

Distal end 16 of shaft 12 includes a bifurcated portion including first and second flanges 16a and 16b, respectively, that define a channel 16c therebetween for receiving jaw members 110 and 120. Each flange 16a, 16b defines a pivot aperture 17a and 17b, respectively, therethrough for receipt of pivot pin 95 and a longitudinal cam slot 18. During assembly, pivot pin 95 is inserted through pivot aperture 17a of flange 16a of shaft 12, pivot aperture 124a of proximal flange 123 of jaw member 120, pivot aperture 173a of first half 170a of knife guide 170, pivot aperture 173b of second half 170b of knife guide 170, pivot aperture 114a of proximal flange 113 of jaw member 110, and pivot aperture 17b of flange 16b of shaft 12 to pivotably engage jaw members 110, 120 at distal end 16 of shaft 12. Angled cam slots 114b, 124b of jaw members 110, 120, longitudinal cam slots 172a, 172b of first and second halves 170a, 170b of knife guide 170, and longitudinal cam slots 18 of flanges 16a, 16b of shaft 12 are configured to receive drive pin 139, which is engaged to drive sleeve 132 at the distal end thereof. As such, upon translation of drive sleeve 132, drive pin 139 is translated along slots 114b, 124b, 172a, 172b, and 18 to pivot jaw members 110, 120 relative to one another between the spaced-apart position (FIG. 1A) and the approximated position (FIG. 1B).

Knife 190 is configured for reciprocation through shaft 12 and knife channels 125 of jaw member 110 and/or jaw member 120 between a retracted position, wherein knife 190 is positioned proximally of distal jaw portions 111, 121 of jaw members 110, 120, respectively, and an extended position, wherein knife 190 extends at least partially through knife channels 125 and between jaw members 110, 120 to cut tissue grasped therebetween. Knife 190 includes a distal blade 191 configured to facilitate cutting tissue upon translation of knife 190 between jaw members 110, 120, and an elongated body portion 192. Body portion 192 of knife 190 defines a longitudinal slot 192a extending therethrough that is configured to receive pivot pin 95 and drive pin 139 to permit translation of knife 190 about pivot pin 95 and drive pin 139. The proximal end of knife 190 defines one or more pin holes 192b therethrough for engaging knife 190 to knife drive rod 193, although other configurations are also contemplated. Knife drive rod 193 is selectively translatable, e.g., upon actuation of trigger 72 of trigger assembly 70, through shaft 12 and relative to end effector assembly 100 to translate knife 190 between the retracted and extended positions.

Referring still to FIGS. 1A-3, and to FIG. 3 in particular, movable handle 40 includes a lever 42 defining a finger hole 43 and a bifurcated arm 46 extending upwardly from lever 42 and into housing 20. Arm 46 is bifurcated to define first and second spaced-apart flanges 46a, 46b, respectively, that are pivotably coupled to housing 20 at the free ends thereof via pivot pin 45. Flanges 46a, 46b extend on either side of drive assembly 41 and are coupled thereto to facilitate movement of jaw members 110, 120 between the spaced-apart position and one or more approximated positions. More specifically, flanges 46a, 46b extend upwardly on either side of mandrel 48 and are disposed within lateral slots 49 defined within mandrel 48. Mandrel 48, in turn, is engaged about drive sleeve 132 such that, upon pivoting of movable handle 40 about pivot pin 45 and relative to fixed handle 50 from an initial position to a compressed position, mandrel 48 and drive sleeve 132 are translated proximally, thereby translating drive pin 139 proximally along angled cam slots 114b, 124b of jaw members 110, 120, respectively, (and cam slots 18 and 170a, 170b of shaft 12 and knife guide 170, respectively) to pivot jaw members 110, 120 from the spaced-apart position (FIG. 1A) to the approximated position (FIG. 1B) to grasp tissue therebetween. On the other hand, return of movable handle 40 towards the initial position returns mandrel 48 and drive sleeve 132 distally, thereby returning jaw members 110, 120 towards the spaced-apart position. A spring (not explicitly shown) may be provided for biasing mandrel 48 distally, thereby biasing movable handle 40 towards the initial position and jaw members 110, 120 towards the spaced-apart position.

As best shown in FIG. 3, a control member 150 pivotably engaged to mandrel 48 and engaged to housing 20 via a pin-slot engagement 152 is also be provided for inhibiting actuation of trigger assembly 70 when jaw members 110, 120 are disposed in the spaced-apart position, e.g., when movable handle 40 is disposed in the initial position (FIG. 1A). More specifically, control member 150 is pivotable relative to mandrel 48 and is rotatable and translatable relative to housing 20 about pin-slot engagement 152 between a blocking position, when movable handle 40 is disposed in the initial position and jaw members 110, 120 are disposed in the spaced-apart position, wherein proximal finger 154 of control member 150 interferes with base 74 of trigger assembly 70 to inhibit actuation of trigger 72 and distal advancement of knife 190, and an unblocking position, when movable handle 40 is disposed in the compressed position and jaw members 110, 120 are disposed in the approximated position, wherein control member 150 is rotated and translated our of the way of base 74, as shown in FIG. 3, such that proximal finger 154 no longer interferes with base 74 of trigger assembly 70, thereby permitting actuation of trigger 72 to deploy knife 190 to the extended position.

Figure 4:
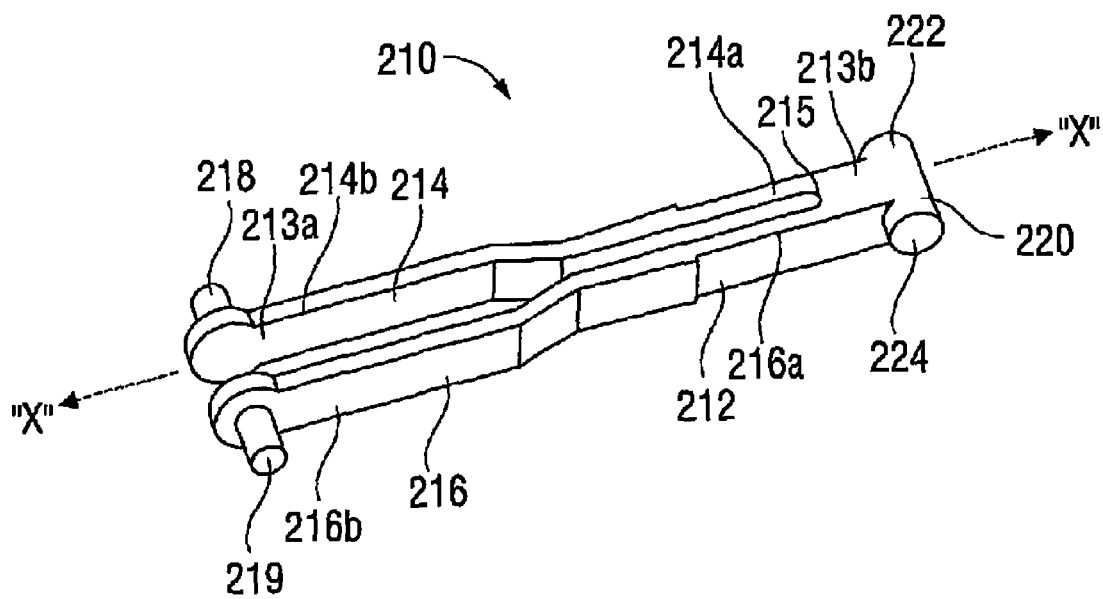
FIG. 4 is a perspective view of a latch arm of the latch assembly of the forceps of FIG. 1A.
Figure 5:
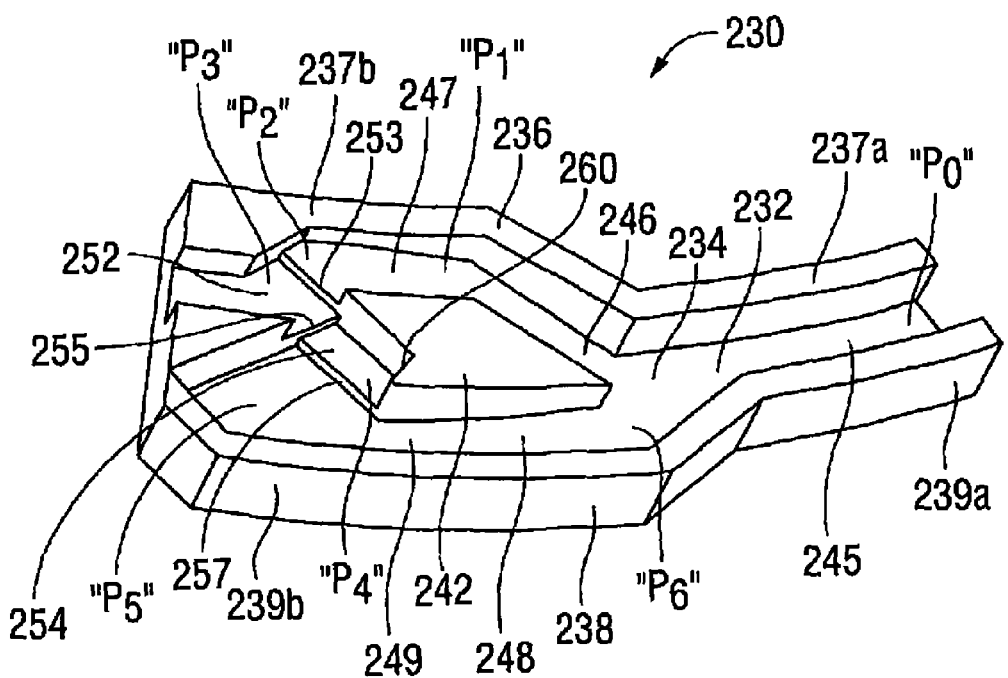
FIG. 5 is a perspective view of one half of a latch block of the latch assembly of the forceps of FIG. 1A.

Turning now to FIGS. 3-5, in conjunction with FIGS. 1A-2, one embodiment of a latch assembly 200 configured for use with forceps 10, or any other suitable surgical instrument, for latching movable handle 40 in the compressed position, thereby latching jaw members 110, 120 in the approximated position, is shown. Latch assembly 200 generally includes a latch arm 210 coupled to movable handle 40 and a latch block 230 engaged to housing 20, although the reverse configuration, e.g., wherein latch block 230 is engaged to movable handle 40 and latch arm 210 is coupled to housing 20, or other similar configurations, are also contemplated.

Referring to FIG. 4, in conjunction with FIG. 3, latch arm 210 includes an elongated body 212 defining a longitudinal axis "X-X" and having a proximal end 213a and a distal end 213b. Distal end 213b of elongated body 212 includes a transverse pin 220 monolithically formed therewith, or otherwise engaged thereto that is configured to pivotably engage latch arm 210 to movable handle 40. More specifically, the inner-facing surfaces of flanges 46a, 46b of bifurcated arm 46 of movable handle 40 each define a cylindrical-shaped recess 47 therein that is configured to receive one of the ends 222, 224 of transverse pin 220 of latch arm 210 therein for pivotably coupling latch arm 210 and movable handle 40 to one another. In other words, transverse pin 220 functions as the pivot point for pivoting of latch arm 210 relative to movable handle 40.

Elongate body 212 of latch arm 210 is bifurcated such that elongated body 212 is substantially divided into first and second spaced-apart fingers 214, 216, respectively, substantially along the length thereof. Fingers 214, 216 are resiliently coupled to one another at fixed ends 214a, 216a, respectively, thereof via a living hinge 215 or other suitable mechanism. Thus, fingers 214, 216 are resiliently flexible relative to one another about living hinge 215 between a neutral position, wherein living hinge 215 biases fingers 214, 216 to extend in substantially parallel, spaced-apart relation relative to one another and about longitudinal axis "X-X," and a loaded position, wherein free ends 214b, 216b of fingers 214, 216, respectively, are urged towards one another (and inwardly towards longitudinal axis "X-X") to closely approximate or abut one another, against the bias of living hinge 215. To achieve and/or maintain this loaded position, as can be appreciated, sufficient inward force acting on fingers 214, 216, respectively, is required to counteract the bias of living hinge 215, which biases fingers 214, 216 towards the neutral position.

With continued reference to FIG. 4, free ends 214b, 216b of fingers 214, 216, respectively, each further include a peg 218, 219, respectively, monolithically formed therewith, or otherwise engaged thereto. Pegs 218, 219 extend outwardly from respective free ends 214b, 216b of fingers 214, 216 in substantially perpendicular orientation relative to fingers 214, 216 and longitudinal axis "X-X." As such, in the neutral position of fingers 214, 216, pegs 218, 219, respectively, extend a relatively greater radial, or transverse, distance from longitudinal axis "X-X" as compared to the loaded position, wherein pegs 218, 219, extend a relatively smaller transverse distance from longitudinal axis "X-X." As will be described in greater detail below, pegs 218, 219 of latch arm 210 are operably engagable within latch block 230 (FIG. 5) and are movable relative to latch block 230 (FIG. 5) in three-dimensions, thus facilitating the latching of movable handle 40 in the compressed position.

Referring to FIG. 5, in conjunction with FIGS. 3-4, latch assembly 200, as mentioned above, includes a latch block 230 fixedly engaged to housing 20. Latch block 230 is formed from a substantially rigid material that resists deformation and defines and substantially encloses a three-dimensional guide track 232 therein that operably engages pegs 218, 219 of latch arm 210 therein for latching movable handle 40 in the compressed position. However, in order to show the features of the internally-disposed, three-dimensional guide track 232 defined within latch block 230, half of latch block 230 has been removed. The halves of latch block 230 are mirror-images of one another and cooperate to form the full latch block 230, thus defining the substantially enclosed, three-dimensional guide track 232 therein. As such, guide track 232 defines a symmetrical configuration about the plane defined between the first and second halves of latch block 230. Thus, although only one half of latch block 230 is shown, it is understood that both halves of latch block 230 cooperate to define guide track 232. The first and second halves of latch block 230 may be monolithically formed or may be engaged to one another in any other suitable fashion, e.g., adhesion, snap-fitting, etc. As will be described in greater detail below, and as mentioned above, pegs 218, 219 of latch arm 210 are operably engaged within and are configured for translation through and three-dimensional movement relative to guide track 232 of latch block 230 to latch, retain, and unlatch movable handle 40 in the compressed position.

With continued reference to FIG. 5, in conjunction with FIGS. 3-4, three-dimensional guide track 232 is defined by cooperating recesses formed within each of the latch block halves of latch block 230 that cooperate to define the substantially enclosed guide track 232. More specifically, guide track 232 is defined within latch block 230 by first and second outer walls 236, 238, respectively, and an inwardly-protruding island 242 extending from each of the latch block halves of latch block 230. Guide track 232 is configured to guide movement of pegs 218, 219 of fingers 214, 216, respectively, of latch arm 210 therethrough to latch and unlatch movable handle 40 in the compressed position, as will be described below.

Distal portions 237a, 239a of first and second outer walls 236, 238, respectively, cooperate to define a chute 245. In the initial position of movable handle 40, pegs 218, 219 of fingers 214, 216, respectively, of latch arm 210 are disposed within chute 245. That is, pegs 218, 219 are initially disposed at (and ultimately return to) position "$P_0$," wherein pegs 218, 219 are disposed within chute 245 towards the distal end thereof. Proximal portions 237b, 239b of first and second outer walls 236, 238, respectively, on the other hand, are further spaced-apart from one another as compared to distal portions 237a, 239a to define body 234 of guide track 232. Islands 242 are disposed within body 234 of guide track 232 and cooperate to define a distal-to-proximal latching path 246, through which pegs 218, 219 travel to latch movable handle 40 in the compressed position, and a proximal-to-distal return path 248, through which pegs 218, 219 of latch arm 210 return upon unlatching and return of movable handle 40 to the initial position. As will be described in greater detail below, the interior surfaces of latch block 230 that define guide track 232 include various different sloped configurations and include various different steps to facilitate the movement of pegs 218, 219 through guide track 232, thus facilitating the engagement and disengagement of latch assembly 200 to latch and unlatch movable handle 40 in the compressed position.

Continuing with reference to FIG. 5, in conjunction with FIGS. 3-4, the track surfaces that define chute 245 define generally flat configurations, although other configurations are contemplated. Track surfaces 247 (or at least portions thereof), which extend proximally from chute 245 to define latching path 246 between islands 242 and proximal portions 237b of first outer walls 236, define sloped configurations such that the height dimension of latching path 246 shallows distally to proximally. Similarly, track surface 249 (or a portion thereof), which extends distally between island 242 and proximal portion 239b of second outer wall 238, ultimately extending to chute 245 to define return path 238, defines a sloped configuration that shallows proximally to distally. However, the slope of track surface 247 of latching path 246 is greater than the slope of track surface 249 of return path 248 and/or the sloped portion of track surface 247 of latching path 246 is greater in length than the sloped portion of track surface 249 of return path 248, such that the proximal end (e.g., the most shallow portion) of track surface 247 of latching path 246 is more shallow than, e.g., elevated relative to, the proximal end (e.g., the most shallow portion) of track surface 249 of return path 248.

A plurality of landings, e.g., first and second landings 252, 254, respectively, and a plurality of steps, e.g., first, second, and third steps 253, 255, 257, respectively, interconnect the proximal ends of latching path 246 and the proximal end of return path 248 to complete guide track 232. More specifically, first step 253 faces generally proximally and interconnects the proximal end of track surface 247 of latching path 246 and the relatively more-recessed track surface of first landing 252. Second step 255 faces generally distally and interconnects the track surface of first landing 252 and the relatively more-recessed track surface of second landing 254. Third step 257 faces generally proximally and interconnects the track surface of second landing 254 and the relatively more-recessed proximal end of track surface 249 return path 248. Further, island 242 includes a notch 260 defined therein that is positioned adjacent second landing 254 for receipt of one of pegs 218, 219 of fingers 214, 216, respectively, of latch arm 210 therein to latch movable handle 40 in the compressed position.

The use and operation of latch assembly 200 in conjunction with forceps 10 for grasping tissue between jaw members 110, 120 and latching jaw members 110, 120 about tissue grasped therebetween, e.g., for subsequently treating and/or dividing tissue, is described with reference to FIGS. 1A-5. Additional features of latch assembly 200 will also become apparent in view of the following description of the use and operation thereof.

Initially, with jaw members 110, 120 disposed in the spaced-apart position (see FIG. 1A), forceps 10 is manipulated and/or maneuvered into position such that tissue to be grasped, treated, and/or divided in disposed between jaw members 110, 120. At this point, movable handle 40 is disposed in the initial position and, accordingly, pegs 218, 219 of fingers 214, 216, respectively, of latch arm 210 are disposed within chute 245 of latch block 230 at position "$P_0$," with fingers 214, 216 disposed in the neutral position. That is, chute 245 of latch block 230 is sufficiently dimensioned such that, in position "$P_0$," latch arm 210 is disposed in the neutral position.

In order to grasp tissue between jaw members 110, 120, movable handle 40 is compressed, or pulled proximally relative to fixed handle 50 from the initial position towards the compressed position such that jaw members 110, 120 are pivoted relative to one another from the spaced-apart position towards the approximated position, as described above. As movable handle 40 is moved proximally towards the compressed position, latch arm 210 is likewise moved proximally and is rotated about transverse pin 220 and relative to movable handle 40 such that pegs 218, 219 of fingers 214, 216, respectively, of latch arm 210 are translated proximally through the track surfaces defining chute 245 of latch block 230 to track surfaces 247 of latching path 246 defined within latch block 230, e.g., from position "$P_0$" to position "$P_1$." Islands 242 of latch block 230 each define an angled or otherwise-configured distal end that is configured to guide pegs 218, 219 of latch arm 210 during proximal translation thereof from chute 245 to latching path 246 of guide track 232.

Further pivoting of movable handle 40 towards the compressed position, e.g., to move jaw members 110, 120 further towards the approximated position for grasping tissue therebetween, urges latch arm 210 to further rotate about movable handle 40 and translate proximally therewith such that pegs 218, 219 are translated along track surfaces 247 of latching path 246 of guide track 232 from position "$P_1$" to position "$P_2$." Due to the shallowing, sloped configuration of track surfaces 247 of latching path 246, pegs 218, 219 and fingers 214, 216, respectively, of latch arm 210 are urged inwardly towards the loaded position and against the bias of living hinge 215 as pegs 218, 219 are translated proximally through guide track 232. Position "$P_2$," wherein pegs 218, 219 are disposed at the proximal ends of track surfaces 247, is the no-return point for movable handle 40. That is, movable handle 40 may be freely compressed and released up to position "$P_2$" without effecting latching of latch assembly 200. However, once movable handle 40 is compressed sufficiently such that pegs 218, 219 are translated beyond position "$P_2$," movable handle 40 will no longer return to the initial position upon release, but will be latched in the compressed position, as will be described below.

As mentioned above, pivoting of movable handle 40 sufficiently so as to translate pegs 218, 219 through guide track 232 beyond position "$P_2$" inhibits return of movable handle 40 to the initial position. That is, as pegs 218, 219 are translated proximally beyond position "$P_2$," pegs 218, 219 are translated over first steps 253 to first landings 252, corresponding to position "$P_3$." In position "$P_3$," since first landings 252 are relatively deeper than the proximal ends of track surfaces 247, fingers 214, 216 of latch arm 210 are partially returned towards the neutral position, under the bias of living hinge 215. As such, with pegs 218, 219 now further spaced-apart, first steps 253 inhibit pegs 218, 219 from returning distally along latching path 246. Rather, upon release of movable handle 40 once position "$P_3$" has been achieved, the bias of movable handle 40 towards the initial position, pulls movable handle 40 and, thus, latch arm 210 distally such that pegs 218, 219 are translated distally over second steps 255, along second landings 254, and into engagement with notches 260 defined within islands 242 at position "$P_4$," the latched position of latch arm 210.

With latch assembly 200 retaining movable handle 40 in the compressed position and, correspondingly, latching jaw members 110, 120 in the approximated position grasping tissue therebetween, tissue sealing plate 112 and/or tissue sealing plate 122 may be energized, e.g., via actuation of switch 62 of switch assembly 60, to conduct energy between tissue sealing plates 112, 122 and through tissue to treat, e.g., seal, tissue. At the completion of tissue treatment, or where it is only desired to cut tissue, trigger 72 of trigger assembly 70 may be actuated to deploy knife 190 to cut tissue grasped between jaw members 110, 120.

Once the desired grasping, treating, and/or cutting of tissue is complete, latch assembly 200 may be unlatched such that jaw members 110, 120 are returned to the spaced-apart position to release tissue and such that movable handle 40 is returned to the initial position. In order to unlatch latch assembly 200, movable handle 40 is compressed or moved proximally from the compressed position to a release position. As movable handle 40 is moved to the release position, pegs 218, 219 are translated proximally along second landings 254 and over third steps 257 to position "$P_5$" at the proximal end of return path 248. Second steps 255 inhibits pegs 218, 219 from returning to first landing 252, while third steps 257 inhibit pegs 218, 219 from returning to the latched position "$P_4$" within notches 260 of islands 242. Third steps 257, in conjunction with track surfaces 249 of return path 248, which defined sloped configurations, facilitate the return of pegs 218, 219 distally along return path 248 in that fingers 214, 216 of latch arm 210 are permitted to return under the bias of living hinge 215 back towards the neutral position as pegs 218, 219 are translated distally along return path 248. Upon further return of movable handle 40, pegs 218, 219 are translated distally along return path 248 to position "$P_0$," and ultimately, distally through chute 245 back to position "$P_0$," corresponding to the initial position of movable handle 40 and the spaced-apart position of jaw members 110, 120.

Figure 6:
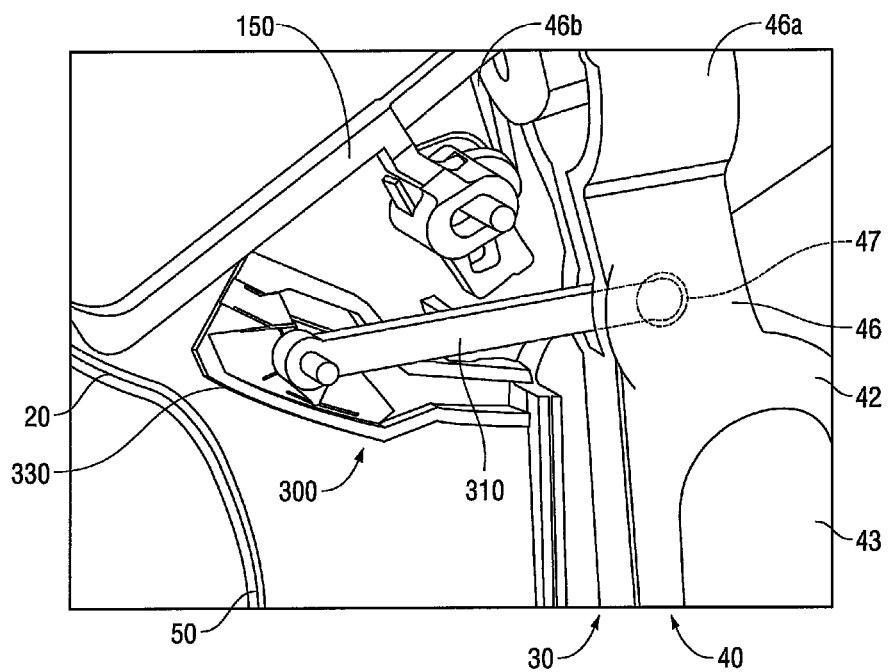
FIG. 6 is a side, perspective view of another latch assembly provided in accordance with the present disclosure and configured for use with the forceps of FIG. 1A.
Figure 7:
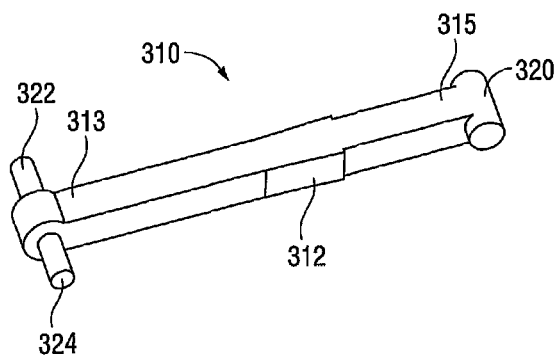
FIG. 7 is a perspective view of a latch arm of the latch assembly of FIG. 6.
Figure 8:
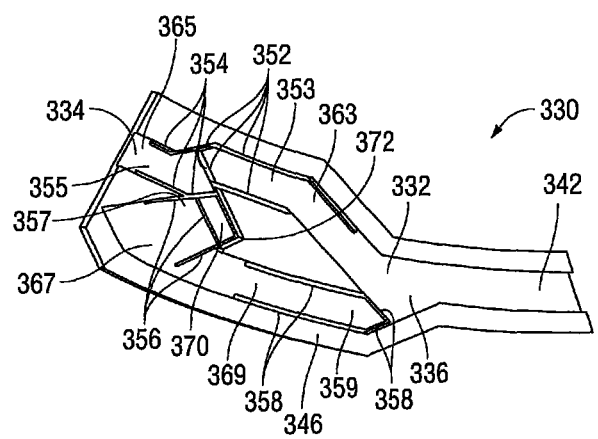
FIG. 8 is a perspective view of one half of a latch block of the latch assembly of FIG. 6.

Turning now to FIGS. 6-8, another embodiment of a latch assembly 300 configured for use with forceps 10 (FIGS. 1A-1B and 2), or any other suitable surgical instrument for latching movable handle 40 in the compressed position, is shown. Latch assembly 300 is similar to latch assembly 200 (FIG. 3) and may include any of the features of latch assembly 200 (FIG. 3), described above. Latch assembly 300 generally includes a latch arm 310 pivotably coupled to movable handle 40 and a latch block 330 disposed within and engaged to housing 20. As will be described in greater detail below, latch arm 310 is pivotable relative to movable handle 40 and is movable relative to latch block 330 and housing 20 as movable handle 40 is moved between the initial and compressed positions to latch and unlatch movable handle 40 in the compressed position and, thus, jaw members 110, 120 (FIGS. 1A-1B) in the approximated position.

With continued reference to FIGS. 6-8, and to FIG. 7 in particular, latch arm 310 includes an elongate body 312 formed from a substantially rigid material and defining proximal and distal ends 313, 315, respectively. Distal end 315 of latch arm 310, similar to latch arm 210 of latch assembly 200 (FIGS. 3-5), includes a transverse pin 320 monolithically formed therewith, or otherwise engaged thereto that is configured to pivotably engage latch arm 310 to movable handle 40, e.g., transverse pin 320 functions as the pivot point for pivoting of latch arm 310 relative to movable handle 40. Proximal end 313 of latch arm 310 includes a pair of laterally-extending pegs 322, 324 extending in opposite, generally perpendicular directions relative to elongate body 312. Pegs 322, 324 may be formed as a single rod extending through a transverse aperture defined within proximal end 313 of latch arm 310, may be monolithically formed with elongate body 312, or may otherwise be configured such that pegs 322, 324 extend from either side of elongated body 312. Similar to pegs 218, 219 of latch arm 210 of latch assembly 200 (FIGS. 3-4), pegs 322, 324 of latch arm 310 of latch assembly 300 are positionable within and are translatable relative to latch block 330 for latching movable handle 40 in the compressed position.

Referring to FIG. 8, in conjunction with FIGS. 6-7, latch block 330 of latch assembly 300 is formed from first and second latch block halves that cooperate to surround proximal end 313 of latch arm 310. The latch block halves are mirror-images of one another, each configured to permit engagement of one of pegs 322, 324 of latch arm 310 therein and to flex upon movement of the respective peg 322, 324 therealong, thus facilitating the latching and unlatching of movable handle 40 in the compressed position, as will be described in greater detail below. Thus, since the latch block halves are mirror images of one another, only one latch block half of latch block 330 is shown herein, keeping in mind that the full latch block 330 is formed from the cooperation of both halves which surround proximal end 313 of latch arm 310 and permit movement of latch arm 310 therebetween.

Each latch block half of latch block 330 includes a body 332 defining proximal and distal ends 334, 336, respectively, a chute 342 extending distally from distal end 336 of body 332, a rim 346 disposed about the outer periphery of body 332, a landing 370 defining a notch 372, and a plurality of sets of slots 352, 354, 356, 358 defined through body 332, each set of slots 352, 354, 356, 358 cooperating to form a resiliently flexible flange 353, 355, 357, 359, that is flexible relative to body 332 about a living hinge 363, 365, 367, 369, respectively. Each flange 353, 355, 357, 359 is flexible relative to body 332 between a neutral position, wherein the respective flange 353, 355, 357, 359 is substantially un-flexed, and a loaded position, wherein the respective flange 353, 355, 357, 359 is flexed against the bias of the respective living hinge 363, 365, 367, 369 to protrude outwardly from body 332. Further, latch block 330 is configured such that, in the neutral positions of flanges 353, 355, 357, 359, the free end of flange 355 is recessed relative to the free end of flange 353, landing 370 is recessed relative to the free end of flange 355, the free end of flange 357 is recessed relative to landing 370, flange 359 is recessed relative to the free end of flange 357, and at least a portion of chute 342 is recessed relative to the free end of flange 359. As will be described in greater detail below, as a result of the above-described configuration, one or more of flanges 353, 355, 357, 359 is selectively flexed from its neutral positions to its loaded positions to facilitate the latching and unlatching of latch arm 310 within latch block 330 and to inhibit backtracking during latching and unlatching.

The use and operation of latch assembly 300 in conjunction with forceps 10 for grasping tissue between jaw members 110, 120 and latching jaw members 110, 120 about tissue grasped therebetween, e.g., for subsequently treating and/or dividing tissue, is described with reference to FIGS. 1A, 1B, 2, and 6-8. The operation of latch assembly 300 is similar to that of latch assembly 200 (FIG. 3) and, thus, similarities therebetween will only be summarily described or omitted entirely. Further, any of the features of latch assembly 200 (FIG. 3), described above, may similarly be provided for use with latch assembly 300, and vice versa.

Initially, with jaw members 110, 120 disposed in the spaced-apart position (see FIG. 1A), forceps 10 is manipulated and/or maneuvered into position such that tissue to be grasped, treated, and/or divided in disposed between jaw members 110, 120. At this point, movable handle 40 is disposed in the initial position and, accordingly, pegs 322, 324 of latch arm 310 are disposed within chute 342 of latch block 330. In this position, flanges 353, 355, 357, and 359 are disposed in their respective neutral positions.

In order to grasp tissue between jaw members 110, 120, movable handle 40 is compressed, or pulled proximally relative to fixed handle 50 from the initial position towards the compressed position such that jaw members 110, 120 are pivoted relative to one another from the spaced-apart position towards the approximated position, as described above. As movable handle 40 is moved proximally towards the compressed position, latch arm 310 is likewise moved proximally and is rotated about transverse pin 320 and relative to movable handle 40 such that pegs 322, 324 of latch arm 310 are translated proximally from chute 342 to and along first flanges 353 of the halves of latch block 330. Translation of pegs 322, 324 along first flanges 353 flexes first flanges 353, against the bias of living hinges 363, outwardly from the neutral position to the loaded position.

Further pivoting of movable handle 40 towards the compressed position, e.g., to move jaw members 110, 120 further towards the approximated position for grasping tissue therebetween, urges latch arm 310 to further rotate about movable handle 40 and translate proximally therewith such that pegs 322, 324 are translated to the free, proximal ends of first flanges 353. This position corresponds to the no-return point for movable handle 40. That is, movable handle 40 may be freely compressed and released up to this point without effecting latching of latch assembly 300. However, once movable handle 40 is compressed sufficiently, e.g., to the compressed position, such that pegs 322, 324 are translated beyond the free ends of first flanges 353, movable handle 40 will no longer return to the initial position upon release, but will be latched in the compressed position, as will be described below.

As mentioned above, pivoting of movable handle 40 sufficiently so as to translate pegs 322, 324 proximally beyond the free ends of first flanges 353 to second flanges 355 inhibits return of movable handle 40 to the initial position. That is, as pegs 322, 324 are translated proximally beyond first flanges 353 to second flanges 355, first flanges 353 are no longer retained in the loaded position, but are returned under the bias of living hinges 363 to the neutral position. This return of first flanges 353 to the neutral position defines a step between first and second flanges 353, 355, respectively, due to the more-recessed configuration of second flanges 355 relative to first flanges 353, thus inhibiting distal return of pegs 322, 324 along first flanges 353. As such, upon release of movable handle 40, due to the bias of movable handle 40 towards the initial position, latch arm 310 is pulled distally such that pegs 322, 324 are translated distally along second flanges 355 flexing second flanges 355 outwardly, ultimately translating distally beyond second flanges 355 to landings 370 and, more specifically, into engagement within notches 372 defined within landings 370 of latch block 330. Once translated distally beyond second flanges 355 to landings 370, second flanges 355 return to their neutral positions under the bias of living hinges 365, defining a step between second flanges 355 and landings 370 to inhibit backtracking of latch arm 310.

With pegs 322, 324 engaged within notches 372 of landings 370, latch arm 310 is disposed in the latched position. In the latched position, movable handle 40 is retained in the compressed position and, correspondingly, jaw members 110, 120 are latched in the approximated position grasping tissue therebetween. As such, tissue sealing plate 112 and/or tissue sealing plate 122 may be energized, e.g., via actuation of switch 62 of switch assembly 60, to conduct energy between tissue sealing plates 112, 122 and through tissue to treat, e.g., seal, tissue. At the completion of tissue treatment, or where it is only desired to cut tissue, trigger 72 of trigger assembly 70 may be actuated to deploy knife 190 to cut tissue grasped between jaw members 110, 120.

Once the desired grasping, treating, and/or cutting of tissue is complete, latch assembly 300 may be unlatched such that jaw members 110, 120 are returned to the spaced-apart position to release tissue and such that movable handle 40 is returned to the initial position. In order to unlatch latch assembly 300, movable handle 40 is compressed or moved proximally from the compressed position to a release position. As movable handle 40 is moved to the release position, pegs 322, 324 are translated proximally from landings 370 to third flanges 357, flexing third flanges 357 outwardly. Translation of pegs 322, 324 to third flanges 357 to effect outward flexing of third flanges 357 defines a step between third flanges 357 and landings 370, thus inhibiting return of pegs 322, 324 into engagement with notches 372. Rather, upon release of movable handle 40 once the release position has been achieved, pegs 322, 324 are translated distally from third flanges 357 to fourth flanges 359 and are translated thereaelong, ultimately returning to the initial position within chute 342.

Similarly as above with respect to the other positions of latch arm 310, third and fourth flanges 357, 359, respectively, are flexed upon translation of pegs 322, 324 therealong and, upon translation of pegs 322, 324 therebeyond, are returned to their respective neutral positions to define steps that inhibit backtracking of latch arm 310. Ultimately, pegs 322, 324 are returned to the initial position within chute 342 and, correspondingly, movable handle 40 is returned to the initial position and jaw members 110, 120 are returned to the spaced-apart position.

Figure 9:
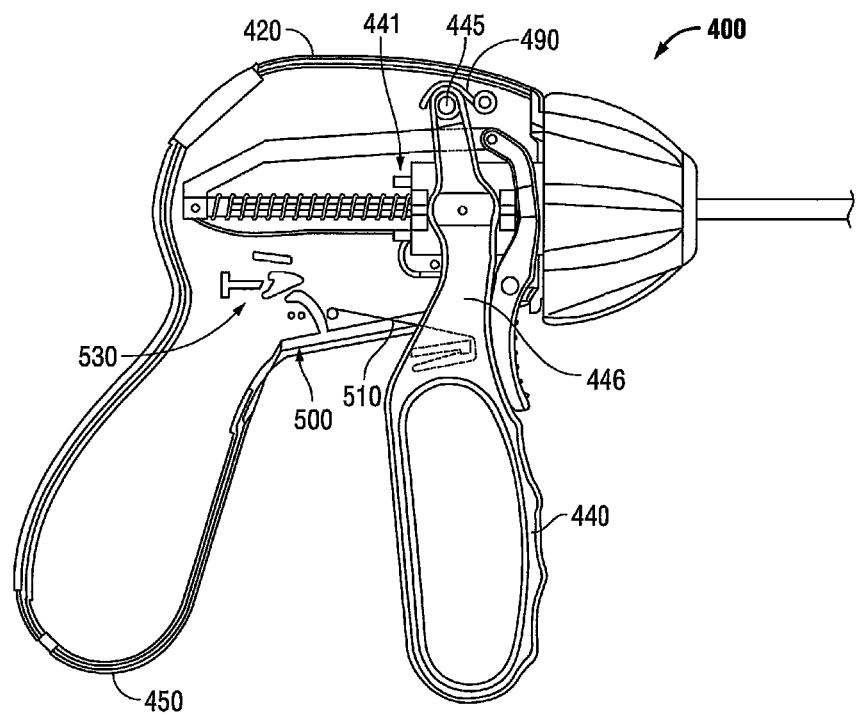
FIG. 9 is a side view of a proximal end of a forceps including another latch assembly provided in accordance with the present disclosure wherein a portion of a housing has been removed to show the latch assembly and other internal components thereof.
Figure 10:
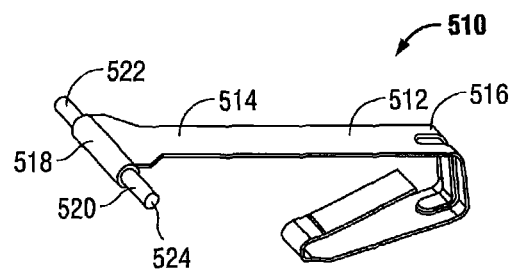
FIG. 10 is a perspective view of a latch arm of the latch assembly of the forceps of FIG. 9.
Figure 11:
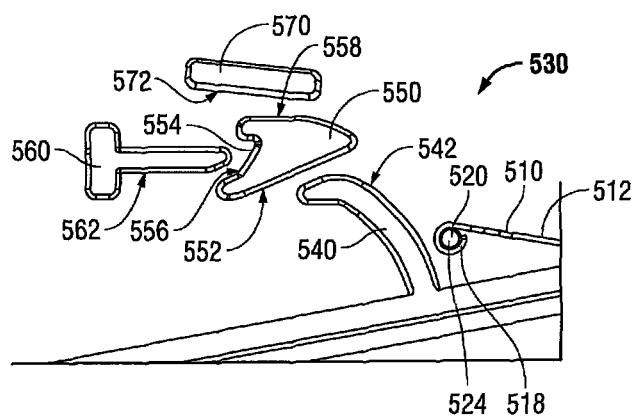
FIG. 11 is a longitudinal, cross-sectional view of ribs of the latch assembly of the forceps of FIG. 9.

Turning now to FIGS. 9-11, another embodiment of a latch assembly 500 configured for use with a forceps 400 (similar to forceps 10 (FIGS. 1A-1B)) or any other suitable instrument including a handle assembly operable to manipulate an end effector assembly, e.g., end effector assembly 100 (FIGS. 1A-1B), thereof. Latch assembly 500 is shown generally including a fixed maze 530 engaged to housing 420 and a latch arm 510 coupled to movable handle 440 and selectively movable through fixed maze 530 for latching and unlatching movable handle 440 in the compressed position and, thus, for latching jaw members 110, 120 of end effector assembly 100 (FIGS. 1A-1B) (or any other suitable end effector assembly of an instrument) in the approximated position.

Forceps 400, similar to forceps 10 (FIGS. 1A-1B and 2), includes a movable handle 440 having a bifurcated arm 446 extending upwardly into housing 420. Arm 446 is bifurcated to engage drive assembly 441 on either side thereof and to permit the pivotable coupling of movable handle 440 to housing 420 via pivot pin 445 such that, upon pivoting of movable handle 440 about pivot pin 445 and relative to fixed handle 440 from an initial position to a compressed position, drive assembly 441 is translated proximally, thereby pivoting jaw members 110, 120 (FIGS. 1A-1B) from the spaced-apart position (FIG. 1A) to the approximated position (FIG. 1B) to grasp tissue therebetween. A spring 490 biases drive assembly 441 distally, thereby biasing movable handle 440 towards the initial position and jaw members 110, 120 (FIGS. 1A-1B) towards the spaced-apart position. Forceps 400 may otherwise be configured similarly to and may contain any of the features of forceps 10 (FIGS. 1A-1B and 2), described above.

With reference in particular to FIGS. 9-10, latch arm 510 is formed from an elongate flat spring 512 or other suitable resiliently flexible member and defines proximal and distal ends 514, 516, respectively. Distal end 516 of latch arm 510 is engaged to movable handle 440. Latch arm 510 extends proximally from movable handle 440 to free, proximal end 514 thereof to define a cantilevered configuration, e.g., where free proximal end 514 is movable relative to distal end 516 upon flexion of flat spring 512 of latch arm 510. Further, proximal end 514 of latch arm 510 defines a transverse tube 518 that is configured to retain an engagement pin 520 therein. Engagement pin 520 defines a length greater than that of transverse tube 518 such that first and second ends 522, 524, respectively, of engagement pin 520 extend at least partially from either end of transverse tube 518. As will be described in greater detail below, first and second ends 522, 524, respectively, of engagement pin 520 are configured to traverse fixed maze 530 to latch and unlatch latch assembly 500 for latching and unlatching movable handle 440 in the compressed position and, thus, for latching and unlatching jaw members 110, 120 (FIGS. 1A-1B) in the approximated position.

Referring again to FIGS. 9-11, and to FIG. 11 in particular, fixed maze 530 includes a plurality of ribs 540, 550, 560, 570 that extend into housing 420 of forceps 400. Housing 420 is formed from first and second housing components (one of which has been removed from FIGS. 9 and 11 to show the internal components of housing 420) that cooperate to define a substantially enclosed cavity configured to house the internal components of forceps 400. Ribs 540, 550, 560, 570 are formed in identical, opposed pairs and extend inwardly from each of the housing components, thus defining three-dimensional fixed maze 530 within housing 420. As a result of this configuration, latch arm 510 is permitted to pass between the opposed pairs of ribs 540, 550, 560, 570, while first and second ends 522, 524, respectively, of engagement pin 520 contact, engage, and/or traverse ribs 540, 550, 560, 570 to latch and unlatch latch assembly 500. Ribs 540, 550, 560, 570 may be monolithically formed with or otherwise engaged to housing 420, e.g., molded into housing 420. Although only one of each pair of ribs 540, 550, 560, 570 is shown and described herein, e.g., for interaction and/or engagement with first end 522 of engagement pin 520, it is understood that the interaction and/or engagement of second end 524 of engagement pin 520 with the other of each pair of ribs 540, 550, 560, 570 is identical to that described below.

With continued reference to FIGS. 9-11, the particular features of fixed maze 530 as well as the use and operation of latching mechanism 500 are described. Referring to FIG. 11 in particular, fixed maze 530 includes a recycle rib 540, a latching rib 550, an over-shoot prevention rib 560, and a return rib 570, each of which is configured to facilitate the latching or unlatching of latch assembly 500 and/or to provide feedback to the user as to the relative position of movable handle 440 with respect to latch assembly 500. The feedback, as will be described below, may be in the form of tactile and/or audible feedback.

Initially, movable handle 440 is disposed in the initial position and, accordingly, jaw members 110, 120 (FIGS. 1A-1B) are disposed in the spaced-apart position. In this position, latch arm 510 is spaced distally from recycle rib 540 of fixed maze 530 of housing 420 and, thus, latch assembly 500 is disengaged, or unlatched.

Referring to FIGS. 9-11, recycle rib 540 defines a generally elongated, angled configuration and is positioned so as to contact first end 522 of engagement pin 520 during actuation of movable handle 440. That is, as movable handle 440 is moved proximally from the initial position, latch arm 510 is likewise moved proximally such that engagement pin 520 is urged into contact with recycle rib 540. Upon such contact, resistance, e.g., tactile feedback, may be felt by the user, e.g., as a result of the flexion of latch arm 510 which is necessary to permit first end 522 of engagement pin 520 to translate proximally along proximal-facing surface 542 of recycle rib 540, thereby allowing further proximal pulling of movable handle 440 towards the compressed position. Recycle rib 540 is configured to guide translation of engagement pin 520 in a generally upward and proximal direction, similar to the direction of movement of movable handle 440 as movable handle 440 is pivoted relative to housing 420 about pivot pin 445.

Upon further actuation of movable handle 440 towards the compressed position, engagement pin 520 of latch arm 510 is translated upwardly and proximally beyond recycle rib 540 and is urged into contact with a first, generally-distally and downwardly-facing surface 552 of latching rib 550. Latching rib 550 includes first surface 552, and also includes an engagement notch 554 defined within a second, proximally-facing surface 556 thereof, and a third, generally upwardly-facing surface 558. First surface 552 of latching rib 550 inhibits further upward advancement of engagement pin 520, thus providing tactile feedback in the form of resistance upon contact of engagement pin 520 with first surface 552 of latching rib 550. With engagement pin 520 disposed in contact with first surface 552 of latching rib 550, further actuation of movable handle 440 urges engagement pin 520 proximally and downwardly along first surface 552 of latching rib 550, thus loading latching arm 510 against the bias of flat spring 512.

Continuing with reference to FIGS. 9-11, once movable handle 440 has been sufficiently actuated such that engagement pin 520 has cleared the proximal end of latching rib 550, engagement pin 520 is urged upwardly under bias, e.g., the loading on engagement pin 520 is released since engagement pin 520 is no longer contacted by first surface 552 of latching rib 550, such that engagement pin 520 is permitted to spring upwardly, ultimately contacting (and producing audible and/or tactile feedback with) first, downwardly-facing surface 562 of over-shoot prevention rib 560. This position corresponds to the compressed position of movable handle 440. In the compressed position, e.g., upon contact of engagement pin 520 with over-shoot prevention rib 560, audible and/or tactile feedback is produced, indicating to the user that movable handle 440 has been sufficiently compressed to achieve a latched condition. That is, prior to engagement pin 520 extending proximally beyond first surface 552 of latching rib 550, e.g., prior to achieving the compressed position, release of movable handle 440 effects return of movable handle 440 to the initial position and jaw members 110, 120 (FIGS. 1A-1B) to the spaced-apart position, both under the bias of spring 590. However, once engagement pin 520 is translated proximally beyond latching rib 550, proximal return of movable handle 440 is inhibited and, rather, as will be described below, engagement pin 520 is urged into engagement with engagement notch 554 defined within latching rib 550.

Once the compressed position is achieved, e.g., once engagement pin 520 contacts over-shoot prevention rib 560 (thus providing audible and/or tactile feedback to the user), movable handle 440 may be released such that movable handle 440 is urged distally under the bias of spring 590 back towards the initial position, thus pulling latch arm 510 distally. As latch arm 510 is pulled distally, engagement pin 520 is translated distally along first surface 562 of over-shoot prevention rib 560, which guides engagement pin 520 towards and, ultimately, into engagement with engagement notch 554 defined within latching rib 550. Engagement of engagement pin 520 within engagement notch 554 inhibits further distal translation of latch arm 510 and, thus, movable handle 440, thereby latching movable handle 440 in the compressed position and latching jaw members 110, 120 (FIGS. 1A-1B) in the approximated position. This corresponds to the latched position of latch assembly 500.

With latch assembly 500 retaining movable handle 440 in the compressed position and, correspondingly, latching jaw members 110, 120 (FIGS. 1A-1B) in the approximated position grasping tissue therebetween, end effector assembly 100 (FIGS. 1A-1B) may be operated to treat and/or cut tissue grasped therebetween, similarly as described above with respect to forceps 10 (FIGS. 1A-1B).

Once the desired grasping, treating, and/or cutting of tissue is complete, latch assembly 500 may be unlatched such that jaw members 110, 120 (FIGS. 1A-1B) are returned to the spaced-apart position to release tissue and such that movable handle 440 is returned to the initial position. In order to unlatch latch assembly 500, movable handle 440 is compressed or moved proximally from the compressed position to a release position. More specifically, as movable handle 440 is compressed to the release position, latch arm 510 is translated proximally such that flat spring 512 is flexed against it bias prior to engagement pin 520 disengaging from notch 554 of latching rib 550. Upon disengagement of engagement pin 520 from latching rib 550, flat spring 512 is unloaded, or returned toward its biased position such that engagement pin 520 is urged into contact with surface 572 of return rib 570. The contact of engagement pin 520 with surface 572 of return rib 570 provides audible and/or tactile feedback to the user that latch arm 510 has been sufficiently disengaged to permit return of movable handle 440 to the initial position. Thus, upon receiving this feedback, the user may release movable handle 440, allowing movable handle 440 to return under the bias of spring 590 to the initial position and, thus, allowing jaw members 110, 120 (FIGS. 1A-1B) to return to the spaced-apart position.

As can be appreciated, the above-described latch assembly 500 provides feedback to the user indicating when the user has compressed movable handle 440 sufficiently, e.g., to the compressed position, and, thus, can release movable handle 440 to latch jaw members 110, 120 (FIGS. 1A-1B) in the approximated position and, similarly, when the user has compressed movable handle 440 sufficiently from the compressed position, e.g., to the return position, and, thus, can release movable handle 440 to return jaw members 110, 120 (FIGS. 1A-1B) to the spaced-apart position.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a movable handle movable between a first position and a second position for transitioning an end effector assembly between a first state and a second state, the movable handle further movable from the second position to a third position to permit return of the movable handle to the first position; and
    a latch assembly, including:
        a latch arm coupled to the movable handle at a first end thereof and having at least one engagement member disposed at a second end thereof; and
        a latch block defining a guide track therein that is configured to receive the at least one engagement member therein, the guide track including a latching path configured to guide translation of the at least one engagement member therealong upon movement of the movable handle from the first position to the second position, an engagement portion configured to engage the at least one engagement member upon achieving the second position to latch the movable handle in the second position, and a return path configured to guide translation of the at least one engagement member therealong upon movement of the movable handle from the second position to the third position and back to the first position, wherein at least a first step is interdisposed between the latching path and the engagement portion such that, upon movement of the movable handle to the second position, the at least one engagement member is guided into engagement with the engagement portion and is inhibited from returning along the latching path, and wherein at least a second step is interdisposed between the engagement portion and the return path such that, upon movement of the movable handle to the third position, the at least one engagement member is guided along the return path and is inhibited from returning to engagement with the engagement portion.

2. The surgical instrument according to claim 1, wherein the movable handle is coupled to a drive assembly, the movable handle movable from the first position to the second position to translate the drive assembly relative to the end effector assembly to transition the end effector assembly between the first and second states.

3. The surgical instrument according to claim 1, wherein the end effector assembly includes first and second jaw members, at least one of the jaw members movable relative to the other between a spaced-apart position and an approximated position for grasping tissue therebetween.

4. The surgical instrument according to claim 1, wherein the latch arm defines a bifurcated second end including first and second engagement members coupled to one another, the first and second engagement members configured to move relative to one another from a neutral position, wherein the first and second engagement members define a first distance therebetween, to a loaded position, wherein the first and second engagement members define a second distance therebetween, upon translation along the latching path and to return to the neutral position upon traversing the first step.

5. The surgical instrument according to claim 4, wherein the first and second engagement members are configured to move relative to one another from the neutral position to the loaded position upon disengagement from the engagement portion and to return to the neutral position upon traversing the second step.

6. The surgical instrument according to claim 4, wherein the first and second engagement members are coupled via a living hinge configured to bias the first and second engagement members towards the neutral position.

* * * * *